(12) United States Patent
Holmes, Jr. et al.

(10) Patent No.: US 6,569,129 B1
(45) Date of Patent: May 27, 2003

(54) BIOLOGICAL REVASCULARIZATION

(75) Inventors: David R. Holmes, Jr., Rochester, MN (US); Robert S. Schwartz, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 110 days.

(21) Appl. No.: 09/661,439

(22) Filed: Sep. 13, 2000

(51) Int. Cl.$^7$ .............................................. A61M 25/00
(52) U.S. Cl. ................... 604/264; 604/164.06; 604/523
(58) Field of Search ................... 604/264, 265, 604/266, 269, 523, 164.06, 164.07

(56) References Cited

U.S. PATENT DOCUMENTS

| | | | | |
|---|---|---|---|---|
| 5,514,092 A | * | 5/1996 | Forman et al. | 604/266 |
| 5,624,396 A | * | 4/1997 | McNamara et al. | 604/264 |
| 5,628,761 A | * | 5/1997 | Rizik | 604/101 |
| 5,681,344 A | * | 10/1997 | Kelly | 604/281 |
| 5,817,073 A | * | 10/1998 | Krespi | 604/267 |
| 6,096,019 A | * | 8/2000 | Andrews | 604/500 |
| 6,149,641 A | | 11/2000 | Ungs | |
| 6,283,951 B1 | * | 9/2001 | Flaherty et al. | 604/164.13 |

OTHER PUBLICATIONS

Sigrid Nikol, MD, et al., "Gene Therapy for Restenosis: Progress or Frustration?", J. Invasive Cardiology 10(8):506–514, 1998, Health Management Publications, Inc.

Fabio S. Brito Jr, MD, et al., "Patient–Related and Angiographic Predictors of Restenosis After Excimer Laser Coronary Angioplasty", J. Invasive Cardiology 10(3):162–168, 1998, Health Management Publications, Inc.

Corey K. Goldman M.D., Ph,D, et al., "Gene Therapy for Vascular Disease", Society for Vascular Medicine and Biology website, Jun. 29, 2000.

Hideo Tamai, MD, et al., "Impact of Tranilast on Restenosis arter Coronary Angioplasty; Tranilast Restenosis Following Angioplasty Trial (TREAT)", American Heart J. 138(5):968–975, 1999, Mosby–Year Book, Inc.

Hidefumi Ohsawa, MD, et al. "Preventive Effects of an Antiallergic Drug, Pemirolast Potassium, on Restenosis After Percutaneous Transluminal Coronary Angioplasty", American Heart J. 136(6):1081–1087, 1998, Mosby–Year Book, Inc.

Gediminas Cepinskas, et al., "PAF–induced Elastase–dependent Neutrophil Transendothelial Migration is associated with the Mobilization of Elastase to the Neutrophil Surface and Localization to the Migrating Front", Journal of Cell Science 112(12), 1999, Published on May 26, 1999.

Samantha Meese, "Innovative Therapy Treats Restenosis after Angioplasty", Medical Tribune 40(2):2, 1999.

Peter Gonschior MD, "Local Drug Delivery for Restenosis and Thrombosis—Progress?", J. Invasive Cardiology 10(8):528–532, 1998, Health Management Publications, Inc.

David Holmes et al. The PRESTO (Prevention of Restenosis with Tranilast and Outcomes) protocol: A double–blind, placebo–controlled trial, Am. Heart J. 2000; 139:23–31.

* cited by examiner

Primary Examiner—Ronald Capossela
(74) Attorney, Agent, or Firm—Fish & Richardson P.C., P.A.

(57) ABSTRACT

A catheter delivery system for delivering a treatment substance to an occlusion in a lumen of a tubular vessel includes a tubular catheter and a treatment substance. The tubular catheter includes a central lumen passing between a proximal end and a distal end adjacent to an inflatable balloon. The treatment substance is in a form that is configured to be deliverable through the central lumen of the catheter into the lumen of the tubular vessel and to solidify in the vessel.

9 Claims, 9 Drawing Sheets

BIOLOGICAL REVASCULARIZATION

TECHNICAL FIELD

This invention relates to catheter-based systems for treatment of chronic total occlusions in tubular vessels by revascularization of the occlusion.

BACKGROUND

Chronic total occlusions in arteries occlude the lumen and prevent blood from flowing to tissue that is distal to the occlusion. Total occlusions have been treated by using laser energy or an atherectomy device to create a channel through the occlusions, through an endarterectomy procedure to open the occluded artery to remove the occlusion, or bypassing the occlusion in, for example, coronary artery bypass grafting. Each of these methods presents challenges to the physician. In the case of using laser energy or an atherectomy device to create a channel, the delivery of the device may be difficult and the resulting surface does not mimic that of a healthy artery. In the case of a bypass around the occlusion, the physician may use a synthetic graft, a vein graft or an artery graft. Each of these grafts has a limited lifetime. Moreover, a synthetic graft does not have a blood contacting surface with the characteristics of a natural artery and there is a limited supply of suitable homologous vein and artery grafts.

SUMMARY

In one general aspect, a catheter delivery system for delivering a treatment substance to an occlusion in a lumen of a tubular vessel includes a tubular catheter and a treatment substance. The tubular catheter includes a central lumen passing between a proximal end and a distal end adjacent to an inflatable balloon. The treatment substance may be in a form that is configured to be deliverable through the central lumen of the catheter into the lumen of the tubular vessel and to solidify in the vessel.

Embodiments of the catheter delivery system may include one or more of the following features. For example, the treatment substance deliverable using the catheter delivery system may include one or more of a fibrin glue, a biodegradable material that is deliverable in liquid form and solidifies after delivery into the lumen of the tubular vessel, an inflammatory agent, a dissolving agent configured to dissolve the occlusion, an angiogenesis agent for revascularizing the occlusion, an anti-restenosis agent, a gene therapy agent, an anti-coagulant agent, and a curable material. The treatment substance may be in a liquid form or a semi-liquid form. The fibrin glue can function as a vehicle to provide the other treatment substances.

The tubular catheter may further include a light delivery fiber having a distal end adjacent to the distal end of the tubular catheter and a proximal end adjacent to the proximal end of the tubular catheter. The treatment substance may include a light curable material. Providing light to the light delivery fiber cures the light curable material. The inflatable balloon may have a proximal end and a distal end and the distal end of the inflated balloon forms a surface that is generally perpendicular to a longitudinal axis of the tubular vessel. The balloon is radially expanded against the walls of the tubular vessel.

The system may further include a wire having a sharpened tip at a distal end of the wire and configured to be delivered through the tubular catheter. The sheath prevents the sharpened tip from damaging or puncturing the tubular catheter. The system may further include a sheath configured to receive the wire and to pass through the central lumen of the tubular catheter for delivering the wire through the tubular catheter. The system may still further include a second sheath, a second wire and at least one treatment plug. The second wire and the treatment plug are received in the second sheath. The second wire has an end configured to advance the treatment plug through the sheath when the second wire is advanced through the sheath. The treatment plug is delivered by withdrawing the sheath while holding the wire in a fixed position.

The catheter delivery system may further include a wire having a sharpened tip at a distal end of the wire that is deliverable through the tubular catheter into a wall of the tubular vessel. The catheter delivery system may also include a sheath that is configured to receive the wire and to be passed through the central lumen of the tubular catheter for delivering the wire through the tubular catheter. The sheath includes a distal end that is configured to direct the distal end of the wire into the wall of the tubular vessel. The wire may have a curved shape for directing the sharpened tip of the wire into the wall of the tubular vessel.

The catheter delivery system may further include a heating catheter deliverable through the tubular catheter and having a distal end configured to produce a heating effect and the treatment substance may include a heat curable material. The heating catheter may produce a heating effect through RF heating or resistive heating.

Another general aspect includes a method for delivering one or more treatment substances to a lumen of a tubular vessel to treat an occlusion of the tubular vessel. The method includes providing a catheter delivery system including a tubular catheter having an inflatable balloon, inserting the tubular catheter into a mammalian vasculature, advancing the tubular catheter through the vasculature until the tubular catheter is adjacent to the occlusion in the tubular vessel, inflating the inflatable balloon, and injecting a first treatment substance into and through the tubular catheter. The catheter system used in the method includes a tubular catheter having a central lumen passing between a proximal end and a distal end adjacent to the inflatable balloon. The treatment substance is in a form that is configured to be deliverable through the central lumen of the catheter into the lumen of the tubular vessel and to solidify in the vessel. When employing the method, inflating the inflatable balloon creates a first volume within the tubular vessel that is defined between the inflated balloon and the occlusion and injecting treatment substance into and through the tubular catheter substantially fills the first volume with the treatment substance.

Embodiments of the method may include one or more the following features. For example, the method may further include withdrawing the tubular catheter away from the first treatment substance when the first treatment substance has solidified. The method may still further include inflating the inflatable balloon to define a second volume defined between the first treatment substance and the inflated balloon and injecting a second treatment substance into and through the tubular catheter such that the second treatment substance substantially fills the second volume. The second treatment substance is configured to solidify in the second volume. The treatment substance may be in a liquid form or a semi-liquid form.

The method then may still further include withdrawing the tubular catheter from the second treatment substance when the second treatment substance has solidified, inflating the inflatable balloon to define a third volume defined between the second treatment substance and the inflated balloon, and injecting a third treatment substance into and through the tubular catheter such that the third treatment substance substantially fills the third volume, whereby the third treatment substance is configured to solidify in the third volume. This process may be repeated using various treatment substances to form a series of different or repeating treatment substances within the tubular vessel.

The treatment substance delivered in the method may include one or more of a fibrin glue, a biodegradable material that is deliverable in liquid form and solidifies after delivery into the lumen of the tubular vessel, an inflammatory agent, a dissolving agent configured to dissolve the occlusion, an angiogenesis agent, an anti-restenosis agent, a gene therapy agent, an anti-coagulant agent, and a curable material.

The inflatable balloon may have a proximal end and a distal end and the distal end of the balloon forms a surface that is generally perpendicular to a longitudinal axis of the tubular vessel when the balloon is inflated. The tubular catheter may further include a light delivery fiber having a distal end adjacent to the distal end of the tubular catheter and a proximal end adjacent to the proximal end of the tubular catheter and the first treatment substance includes a light curable material such that applying light to the light delivery fiber directs light onto the first treatment substance to cure the light curable material of the first treatment substance.

Another general aspect includes a method for delivering one or more treatment substances to an occlusion in a tubular vessel to treat the occlusion of the tubular vessel. The method includes providing a catheter delivery system for delivering a treatment substance to an occlusion in a lumen of a tubular vessel, the catheter system including: a tubular catheter having a central lumen passing between a proximal end and a distal end adjacent to an inflatable balloon, a wire having a sharpened tip at a distal end of the wire and configured to be delivered through the tubular catheter, and a treatment substance that is configured to be deliverable through the central lumen of the catheter into the occlusion of the tubular vessel. The tubular catheter is inserted into a mammalian vasculature and advanced through the vasculature until the distal end of the tubular catheter is adjacent to the occlusion in the tubular vessel. The balloon is inflated to firmly position the tubular catheter within the tubular vessel. The wire is inserted into the tubular catheter and advanced until the sharpened tip is adjacent to the occlusion in the tubular vessel. The wire then is further advanced such that the sharpened tip is inserted into the occlusion and forms a channel in the occlusion.

Embodiments of the method may include one or more of the following features. For example, a treatment substance may be injected into and through the tubular catheter such that the treatment substance is injected into the channel in the occlusion. The treatment substance may include a material configured to solidify in the channel in the occlusion. The tubular catheter may further include a light delivery fiber having a distal end adjacent to the distal end of the tubular catheter and a proximal end adjacent to the proximal end of the tubular catheter and the treatment substance may include a light curable material such that applying light to the light delivery fiber directs light onto the treatment substance to cure the light curable material of the treatment substance.

The method may further include inserting one or more treatment plugs into the channel in the occlusion and the catheter delivery system further includes a sheath, a second wire and at least one treatment plug. The second wire and the treatment plug are received in the sheath and the second wire has an end that is configured to advance the treatment plug through the sheath when the second wire is advanced through the sheath. Inserting the treatment plug into the channel includes advancing the sheath into the channel, advancing the second wire through the sheath to advance the treatment plug into the channel and withdrawing the sheath while leaving the second wire in a relatively fixed position when the treatment plug is in the channel.

Another general aspect includes a catheter system for delivering a treatment substance into an occlusion in a lumen of a tubular vessel. The catheter system includes a tubular catheter having a lumen passing between a proximal end and a distal end, a wire configured to be passed through the tubular catheter to create a channel in the occlusion, and a treatment substance for delivery through the tubular catheter into the occlusion to treat the occlusion.

The treatment substance delivered with the catheter system may include one or more of a fibrin glue, a biodegradable material that is deliverable in liquid form and solidifies after delivery into the lumen of the tubular vessel, an inflammatory agent, a dissolving agent configured to dissolve the occlusion, an angiogenesis agent, an anti-restenosis agent, a gene therapy agent, an anti-coagulant agent, and a curable material.

The wire may include a distal end having a sharpened tip and a proximal end having a gripping implement. The tubular catheter may include a distal end having a tapered tip and the tapered tip may have an inner diameter that is larger than an outer diameter of the wire. The tapered tip may have at least one eye hole passing through a wall of the tubular catheter.

Another general aspect includes a method of delivering a treatment substance to an occlusion. The method includes providing a tubular catheter having a lumen passing between a proximal end and a distal end, providing a wire having a proximal end and a distal end and being configured to be passed through the tubular catheter to create a channel in the occlusion, providing a treatment substance for delivery through the tubular catheter into the occlusion to treat the occlusion, inserting the tubular catheter into a mammalian vasculature, advancing the tubular catheter through the vasculature until the distal end of the tubular catheter is adjacent to the occlusion, inserting the wire into the tubular catheter, advancing the wire through the tubular catheter until the distal end of the wire is adjacent to the occlusion, further advancing the distal end of the wire into the occlusion to create a channel in the occlusion, withdrawing the wire from the occlusion and the tubular catheter, and injecting a treatment substance through the tubular catheter into the channel in the occlusion.

Embodiments of the method may include one or more of the following features. For example, the treatment substance may include one or more of an angiogenesis agent, a combination of angiogenesis agents, an occlusion dissolving agent, an anti-restenosis agent, and an inflammatory agent. The wire may include a distal end having a sharpened tip and a proximal end having a gripping implement. The tubular catheter may include a distal end having a tapered tip and the tapered tip may have an inner diameter that is larger than an outer diameter of the wire. The tapered tip may have at least one eye hole passing through a wall of the tubular catheter.

In another general aspect, a catheter delivery system for delivering a treatment substance to a lumen of a tubular vessel includes a tubular catheter and an expandable treatment stent. The tubular catheter includes a central lumen passing between a proximal end and a distal end that is adjacent to an inflatable balloon. The expandable treatment stent is mounted to the inflatable balloon for expansion and deployment by the balloon and includes an expandable stent component and a treatment substance component attached to the expandable stent component.

Embodiments of the stent may include one or more of the following features. For example, the treatment substance may include an inflammatory agent, a dissolving agent configured to dissolve the occlusion, at least one angiogenesis agent, an anti-restenosis agent, a gene therapy agent, and an anti-coagulant agent.

The system and methods can provide numerous advantages. For example, delivering the treatment substances and materials can stimulate collateral neo-angiogenesis formations so that distal ischemia can be reduced. The system and methods also can lead to a softening of the occlusion so that subsequently the occlusion can be passed and treated percutaneously with an angioplasty or an atherectomy device after accessing the distal lumen of the occlusion.

The details of one or more embodiments of the invention are set forth in the accompanying drawings and the description below. Other features and advantages of the invention will be apparent from the description and drawings, and from the claims.

DESCRIPTION OF DRAWINGS

Like reference symbols in the various drawings indicate like elements.

DETAILED DESCRIPTION

The inventors have developed methods and devices for treating chronic total occlusions by delivering a plug or formulation that includes a treatment substance into a position that is adjacent to or within the occlusion or by injecting the treatment substance into the occlusion. For example, the plug can include a growth factor substance with angiogenesis properties to stimulate growth of blood vessels throughout the occlusion and a substance to weaken the occlusion. In this manner, substances can be delivered to weaken the occlusion and then revascularize it. The occlusion also can be treated solely by injecting a substance into the occlusion that weakens the occlusion. For example, the substance can be a gene therapy agent that transfects the occlusion and reduces its size. Some of the substances that can be used to weaken the plaque in the occlusion include tranilast, elastase and collagenase. An inflammatory agent that can be used includes copper.

Figure 1:
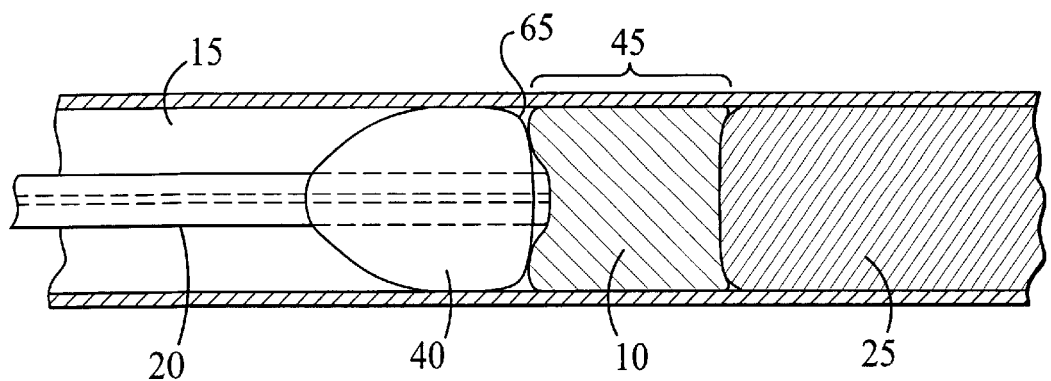
FIG. 1 is a side view of a treatment substance delivery catheter system deployed in an artery adjacent to a total chronic occlusion.
Figure 2:
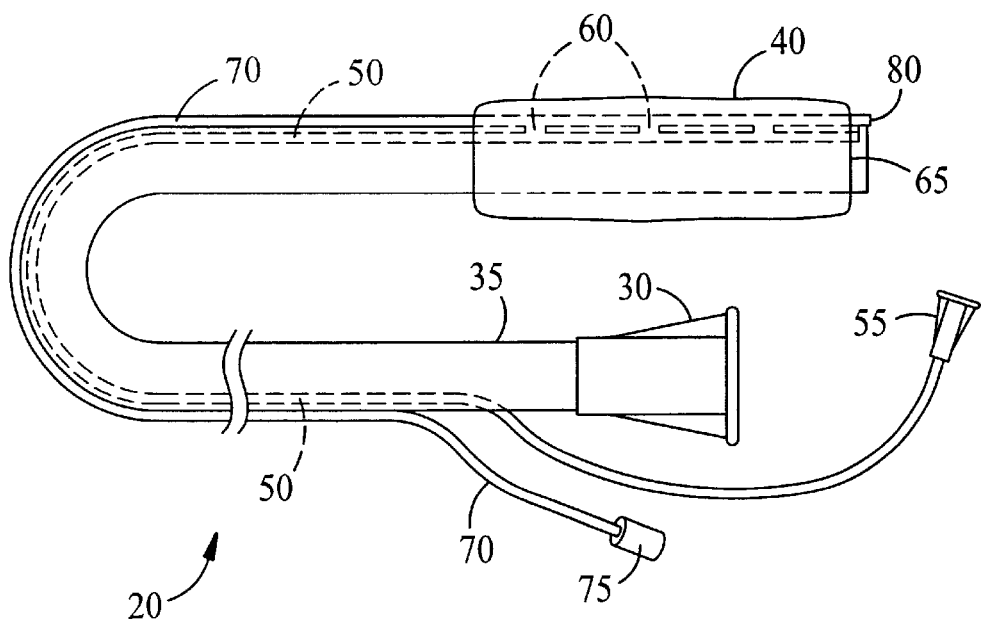
FIG. 2 is a side view of the treatment substance delivery catheter system of FIG. 1.

Referring to FIGS. 1 and 2, a treatment substance 10 can be delivered within an artery 15 through a balloon catheter 20 and cured in place adjacent to and in contact with an occlusion 25. The treatment substance 10 can include one or more of a substance to weaken the occlusion 25, a substance to revascularize the occlusion, a substance to encapsulate the weakening and revascularizing components, a substance that is photocurable, and a substance that will degrade over time. The treatment substance 10 in a liquid form is injected through a hub 30 of the catheter 20 that connects to a main lumen 35 of the catheter 20. An inflatable balloon 40 is inflated to form a region 45 defined between the occlusion 10 and the balloon 40. The balloon 40 is inflated through a channel 50 that passes between a hub 55 and openings 60 from the channel 50 into the balloon. The balloon 40 may have a distal end 65 with a flat or curved shape which will be the reverse of the end of the formed treatment substance 10 when it is cured, i.e., solidified.

When the treatment substance is injected into the region 45 through the catheter 20, it will fill the region and abut the occlusion 25 and the balloon 40. In some embodiments, the treatment substance 10 then is cured by using light provided by a light delivery fiber 70 which passes between an optical connector 75 and a distal end of the fiber 80. The optical connector 75 is connected to an optical light source (not shown) so that light can be selectively delivered at the treatment substance 10 to cure it. After curing, the balloon 40 is deflated and the catheter 20 is withdrawn from the artery 15.

Figure 3:
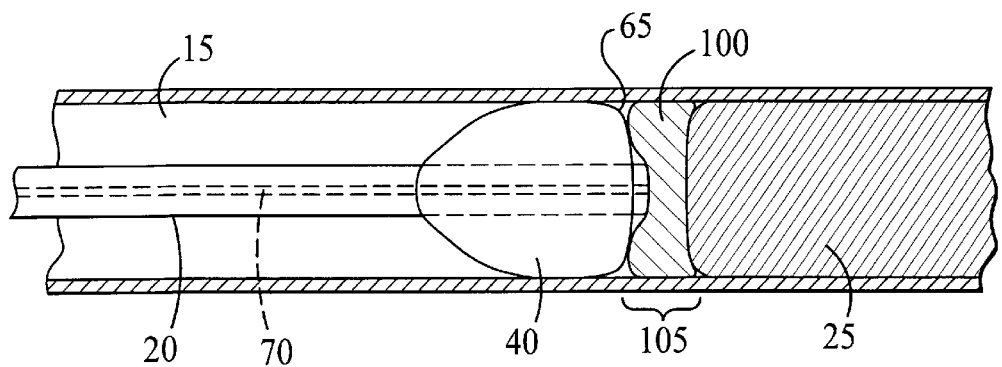
FIGS. 3–6 are side views showing the catheter-based formation of a multi-treatment substance being formed adjacent to the total chronic occlusion of FIG. 1.

Over time, the treatment substance 10 will release the substance to weaken the occlusion and the substance to revascularize the occlusion. In this manner, the occlusion will be replaced with functioning blood vessels that extend through the occlusion. The treatment substance 10 can be tailored to release the substance according to a desired sequence. For example, referring to FIGS. 3–6, the treatment substance 10 can be delivered such that it consists of multiple layers. As illustrated in FIG. 3, the catheter 20 is placed a short distance from the occlusion 25 and a layer of substance 100 is delivered into a region 105 defined between the occlusion and the balloon 40. The layer of substance 100 may include a biodegradable, light curable material that is delivered in liquid form and then cured into a solid form by the delivery of light through the light fiber 70. The layer of substance 100 also may include an agent that causes inflammation or transfection. For example, the agent may be copper, which causes the occlusion to become inflamed upon continuous contact. The agent also may be a virus that has been infected so that it causes the occlusion 25 to be infected upon contact. In either case, the agent will cause an increase in cellular activity in the occlusion 25. As the biodegradable, light curable material degrades over time, it releases or elutes the agent or agents, which will then be in contact with the occlusion 25.

Figure 4:
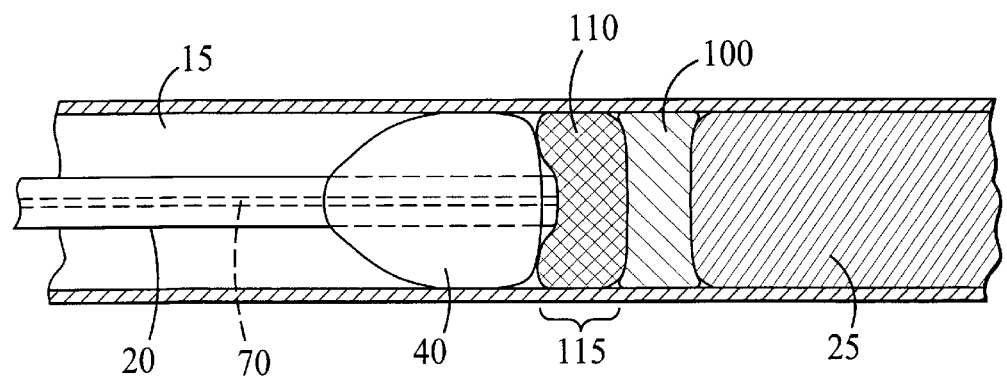

As illustrated in FIG. 4, a second layer of substance 110 is formed adjacent to the first layer 100. To form the second layer of substance 110, the physician cures the first layer and then withdraws the catheter a short distance so that a new region 115 is formed between the balloon 40 and the first layer of substance 100. The physician then injects a substance that fills region 15. The substance may include a biodegradable, light curable material that is delivered in liquid form and then cured into a solid form by the delivery of light through the light fiber 70. Within the light curable material may be an agent that will dissolve the occlusion 25. For example, the agent may be collagenase, elastase or tranilast. As the biodegradable light curable material degrades over time, it releases the dissolving agent, which will then be in contact with the occlusion. With this sequence of substance delivery (i.e., infecting or inflammation agent followed by dissolving agent), the occlusion is thought to be made more susceptible to the dissolving agent that will dissolve the occlusion.

Figure 5:
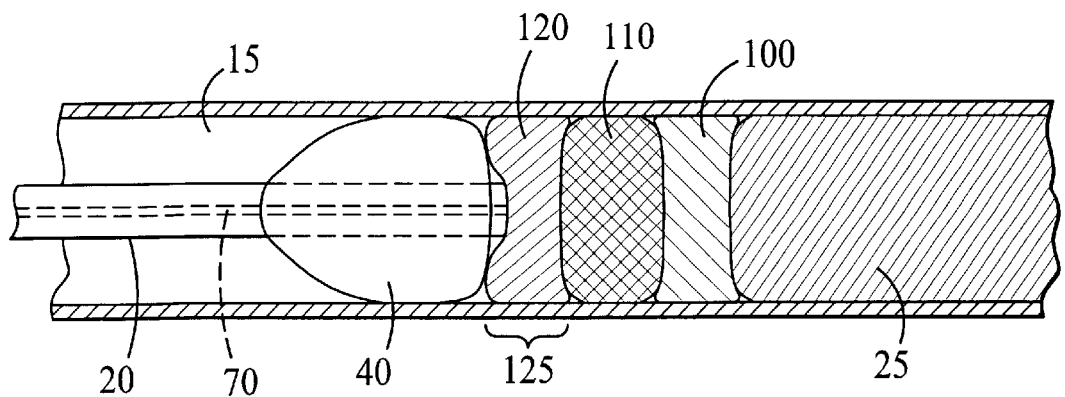

As illustrated in FIG. 5, a third layer of substance 120 is formed adjacent to the second layer 110. To form the third layer of substance 120, the physician cures the second layer of substance 110 and then withdraws the catheter 20 a short distance so that a new region 125 is formed between the balloon 40 and the second layer of substance 110. The physician then injects a substance that fills the region 125. Like the first layer of substance 100 and the second layer of substance 110, the third layer of substance 120 may include a biodegradable, light curable material. It also may include an agent to cause angiogenesis in the occlusion 25 or what remains of the occlusion. Thus, as the biodegradable material in the third layer of substance 120 degrades, the angiogenesis agent is released.

Figure 6:
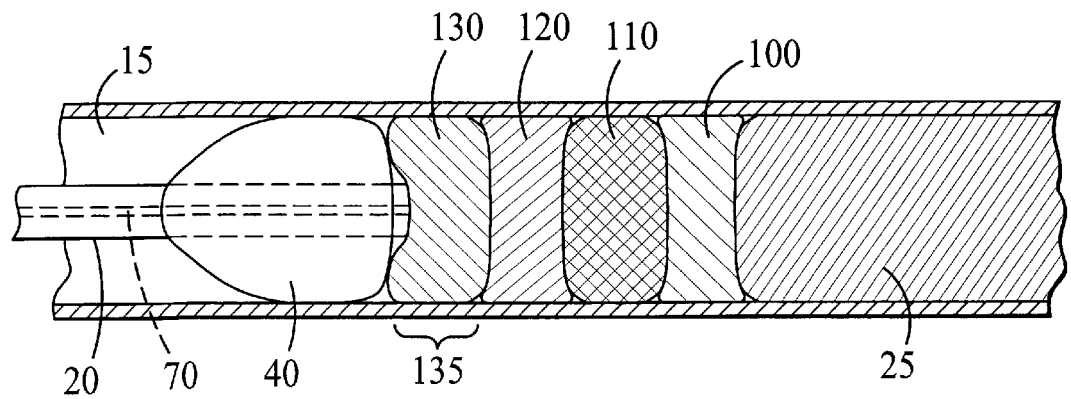

As illustrated in FIG. 6, a fourth layer of substance 130 is formed adjacent to the third layer of substance 120. To form the fourth layer of substance 130, the physician cures the third layer of substance 120 and then withdraws the catheter 20 a short distance so that a new region 135 is formed between the balloon 40 and the third layer of substance 120. The physician then injects a substance that fills the region 135. Like the other layers of substance 100, 110 and 120, the fourth layer of substance 130 may include a biodegradable, light curable material. It also may include an anti-coagulant agent, such as heparin or coumadin to prevent blood clot formations that can occur when blood contacts foreign surfaces, such as the solidified treatment substances. Thus, as the biodegradable material in the fourth layer of substance 130 degrades, the anti-coagulant agent is released and will prevent a new occlusion from forming adjacent to the layers 100, 110, 120 and 130. The fourth layer of substance 130 also may include an agent, such as tranilast or radioactive microspheres, to prevent restenosis of the artery 15 in the region adjacent to the layers 100, 110, 120 and 130.

Although a biodegradable, light curable material can be used to create a drug delivery matrix, other materials can be used, such as fibrin or a fibrin glue. The fibrin is mixed with a treatment agent, such as one or more of those described above, and delivered in the same manner as described above. However, the fibrin does not need light to cure it and, therefore, can be cured without the necessity of providing a curing light.

Although only four layers are illustrated in FIGS. 3–6, more or fewer layers can be formed based on the desired treatment sequence and timing. For example, the sequence can be varied to provide a repetitive delivery of an inflammatory substance and a dissolving substance by forming more than one layer of each substance. Moreover, if desired, each layer can be formed so that it dissolves quickly and releases a large bolus of the treatment agent contained within it. For example, the layers can be narrower and formed with more of the treatment agent. In this manner, the occlusion 20 can be subjected to a large bolus of an inflammatory agent and then shortly thereafter subjected to a large bolus of a dissolving agent. This process can then be continued as desired based on the number of layers formed in the artery 15.

In addition, although each layer was described as containing only one treatment agent, each layer can be tailored to contain multiple treatment agents depending upon the circumstances. For example, the physician may want to include an anti-coagulant or an anti-restenosis agent in each layer along with the dissolving agent or angiogenesis agent.

Finally, the catheter 20 may be modified to cure the treatment substance 10 using methods other than light. For example, the treatment substance 10 can include a heat curable substance and the light delivery fiber 70 can be replaced by a heating element. Following injection of the treatment substance 10, the heating element can be energized to heat and cure the heat curable substance.

Figure 7:
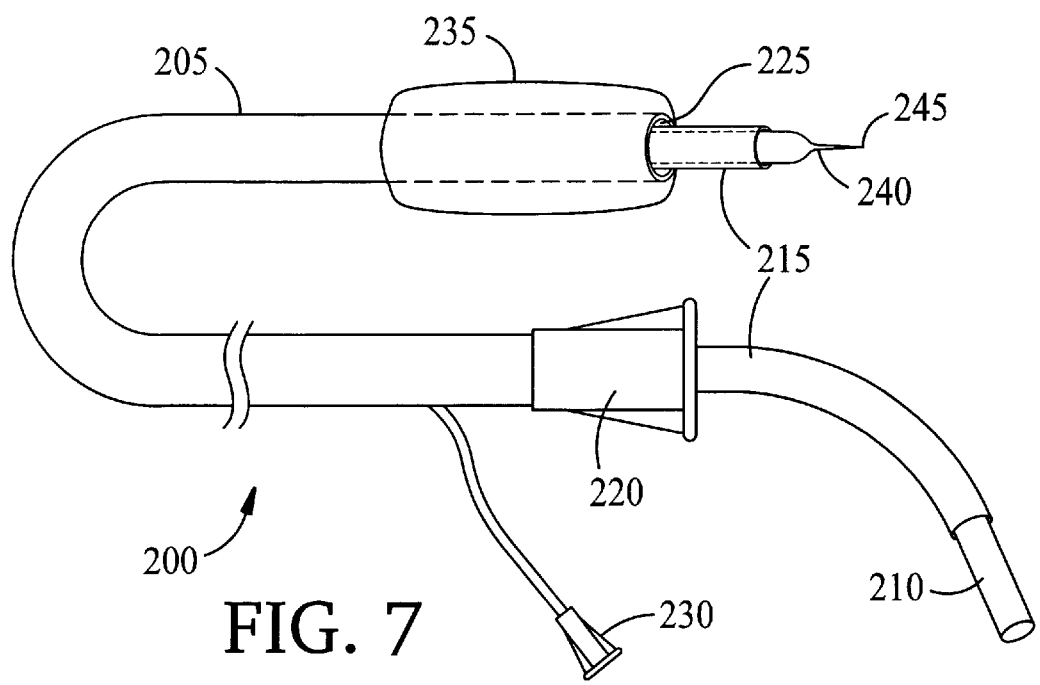
FIG. 7 is a side view of a treatment substance delivery catheter system for treating total chronic occlusions.

Referring to FIG. 7, an injection catheter system 200 includes a catheter 205, a wire 210, and a sheath 215 to enclose the wire. The catheter 205 has a hub 220 that opens to a central lumen 225 of the catheter 205 and through which the wire 210 and sheath 215 are passed. The catheter 205 also includes a hub 230 that is connected to an inflation device (not shown) that is used to inflate an inflatable balloon 235 at the distal end of the catheter. The wire 210 has a distal tip 240 with a sharpened end 245. The sheath 215 encloses the wire 210 and prevents the sharpened end 245 from puncturing the catheter 205 when it is passed through the catheter.

Figure 8:
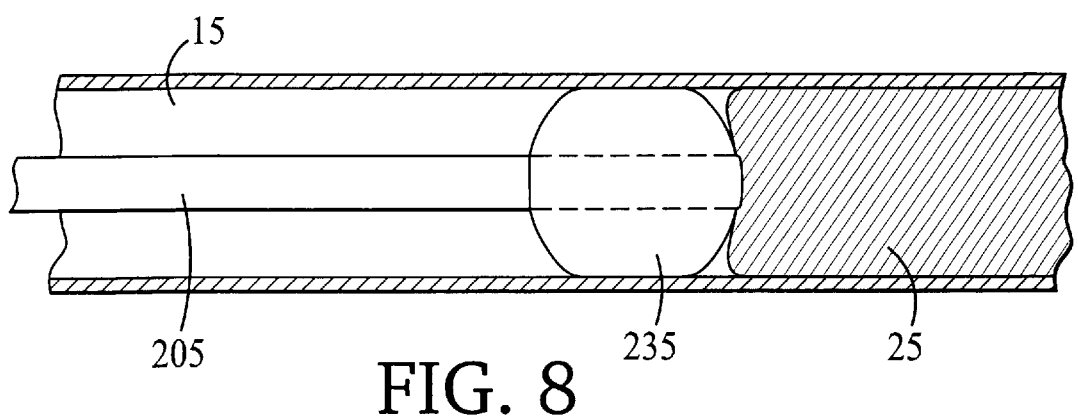
FIGS. 8 and 9 are side views of the catheter system of FIG. 7 showing the delivery of a treatment substance to a total chronic occlusion.
Figure 9:
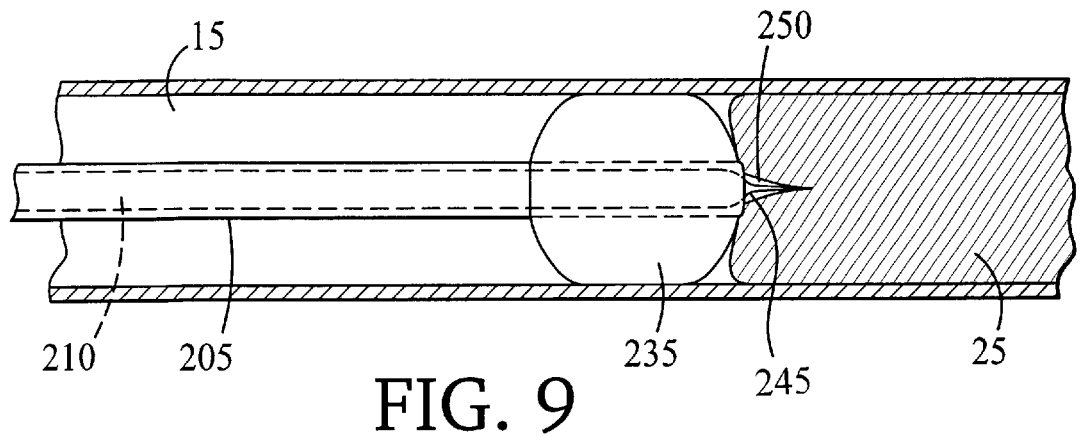

The injection catheter system 200 is used to inject a treatment agent into the chronic total occlusion 25. As illustrated in FIG. 8, the catheter 205 is introduced into the vasculature and delivered to the artery 15 such that the distal end of the catheter is adjacent to the occlusion 25. The inflatable balloon 235 then is optionally inflated to hold the catheter 205 in a fixed position relative to the occlusion 25. The wire 210 then is used to form a channel 250 in the occlusion 25 by advancing the wire to the distal end of the catheter and then pulling back on the sheath to expose the sharpened point 245. The physician then advances the wire 210, which forces the sharpened point 245 into the occlusion. Further advancing the wire 210 will cause the distal end 240 of the wire to further widen and lengthen the channel 250. The physician then completely withdraws the wire 210 and sheath 215 from the catheter 205 while leaving the catheter in the artery 15.

The physician then can deliver a treatment agent to the occlusion. The treatment agent can be an angiogenesis agent, an inflammatory agent, a dissolving agent to dissolve the occlusion, or a virus that will transfect the occlusion through gene therapy techniques. With the balloon inflated, the treatment agent or agents are delivered through the central lumen 225 under pressure, which will force the agent into the channel 250. If the agent has sufficient strength or characteristics, the physician then can conclude the procedure by deflating the balloon 235 and withdrawing the catheter 205 from the artery 15.

Figure 10:
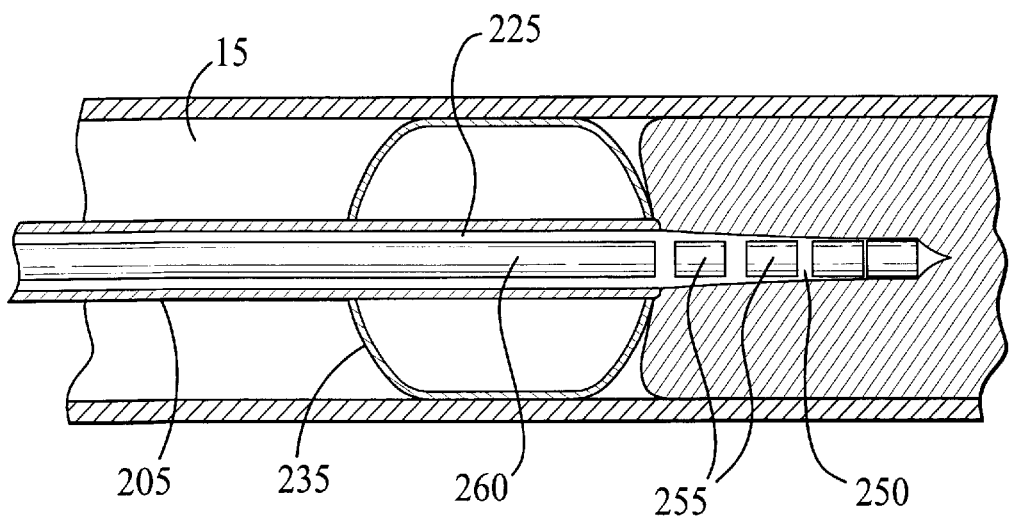
FIG. 10 is a cross-sectional side view of the catheter system of FIG. 7 showing plugs containing the treatment substance being delivered to the total chronic occlusion.

In the event that the physician intends to provide a longer exposure of the occlusion 25 to the treatment agents, the injection catheter system 200 can be modified. For example, referring to FIG. 10, the treatment agents can be in the form of a plug 255. The treatment agents also can be in the form of a sponge or a pledget. To deliver the plug 255, the channel 250 is formed as described above. The wire 210 then is removed and one or more plugs 255 are inserted into the lumen 225 through the hub 220. A delivery wire 260 having a blunt end 265 then is used to advance the plugs 255 through the catheter 205 into the channel 250. By keeping the balloon inflated, the central lumen 225 will remain aligned with the channel 250 so that the delivery wire 260 will force the plugs into the channel.

Figure 11:
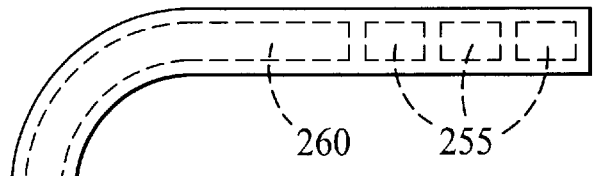
FIG. 11 is a side view of a blunt wire and plugs covered by a sheath for delivery through the catheter system of FIG. 7.

Referring to FIG. 11, the physician can enclose the delivery wire 260 in a sheath 265 and insert the plugs 255 into the sheath. The wire 260, sheath 265, and plugs 255 then can be advanced as one unit through the catheter 205 and into the channel 250. When the plugs 250 are within the channel 250, as can be visualized under fluoroscopy, the physician pulls back the sheath 265 so that the plugs are surrounded by the channel and then withdraws the wire 260. Finally, the catheter 205 is withdrawn. This configuration of the plugs 255. sheath 265 and wire 260 advantageously ensures that the plugs are placed within the channel 250 and do not become loose within the artery 15.

Figure 12:
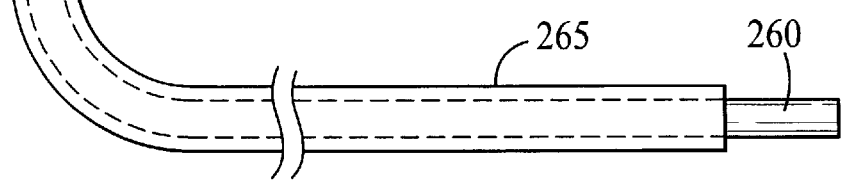
FIG. 12 is a side view of a treatment substance delivery catheter for treating total chronic occlusions in which the treatment substance includes a light curable material.
Figure 12:
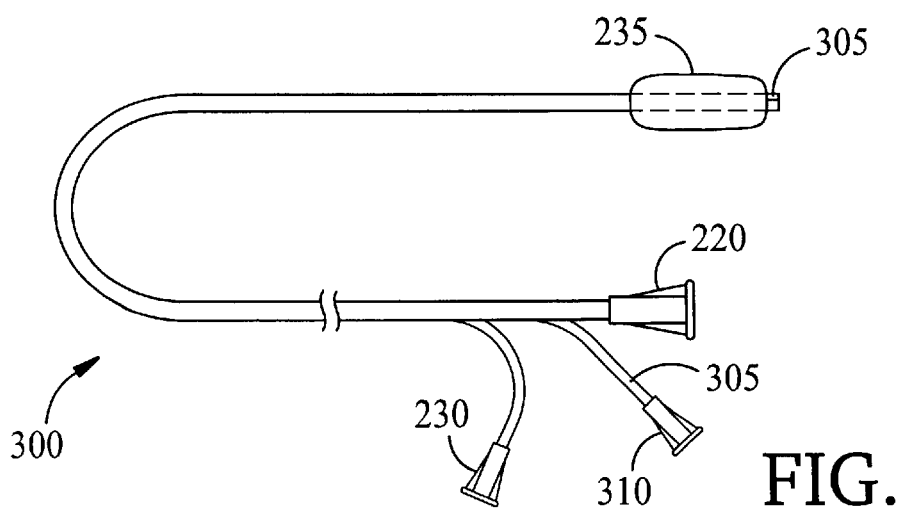

As an alternative to injecting a treatment agent or placing a plug, the physician may intend to inject a treatment substance that includes a biodegradable, light curable material and one or more of a dissolving agent, an inflammatory agent, an angiogenesis agent, an anti-coagulant, and a transfecting agent. Referring to FIG. 12, a catheter 300 for using light to cure a light curable material includes a light fiber 305 that terminates on one end at the distal end of the catheter and on the other end is connected to an optical connector 310. Like the catheter 200 of FIG. 7, the catheter 300 includes the balloon 235, the hub 220 and the hub 230. An optical light source (not shown) can be connected to the optical connector 310 and used to provide light to the fiber 305. The treatment substance can be delivered in the manner described above and then cured by delivering light through the light fiber 305. In this manner, the biodegradable, light curable material will degrade over time and release the treatment agents such that they are in contact with the interior of the occlusion 25 and will revascularize the occlusion.

Figure 13:
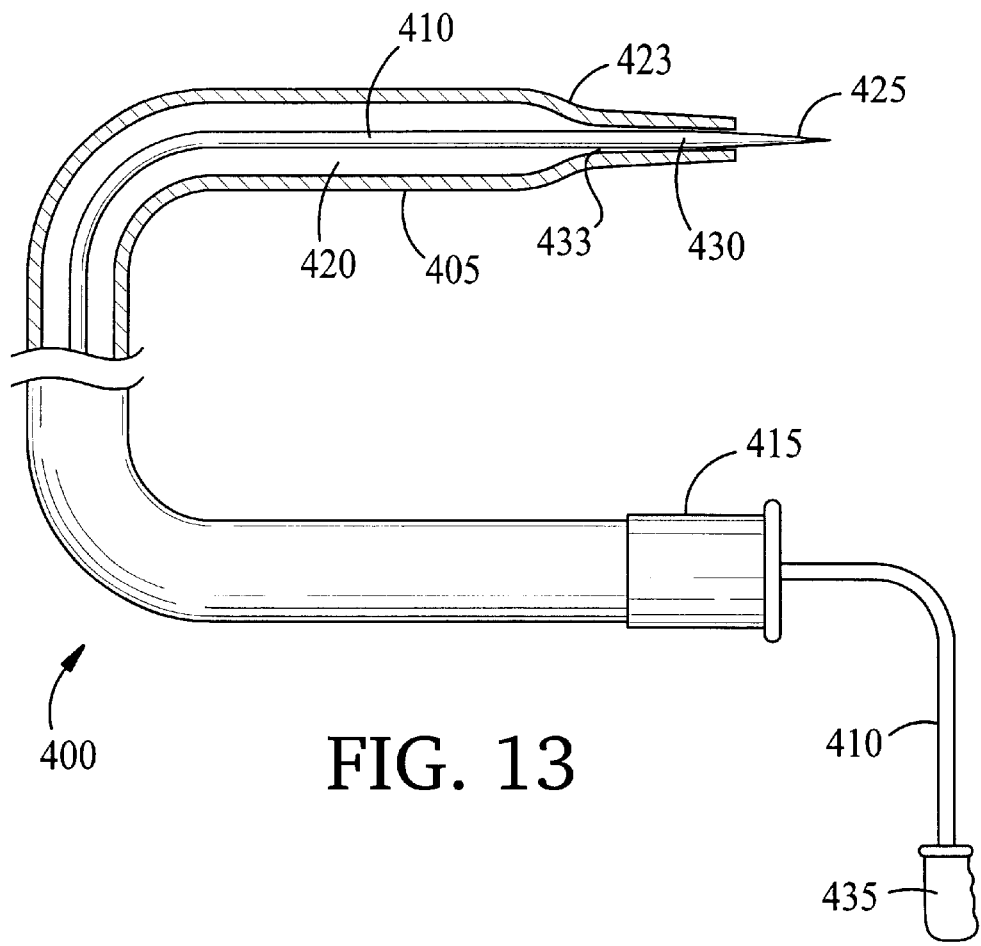
FIG. 13 is a partial cross-sectional side view of a treatment substance injection catheter and a wire.
Figure 14:
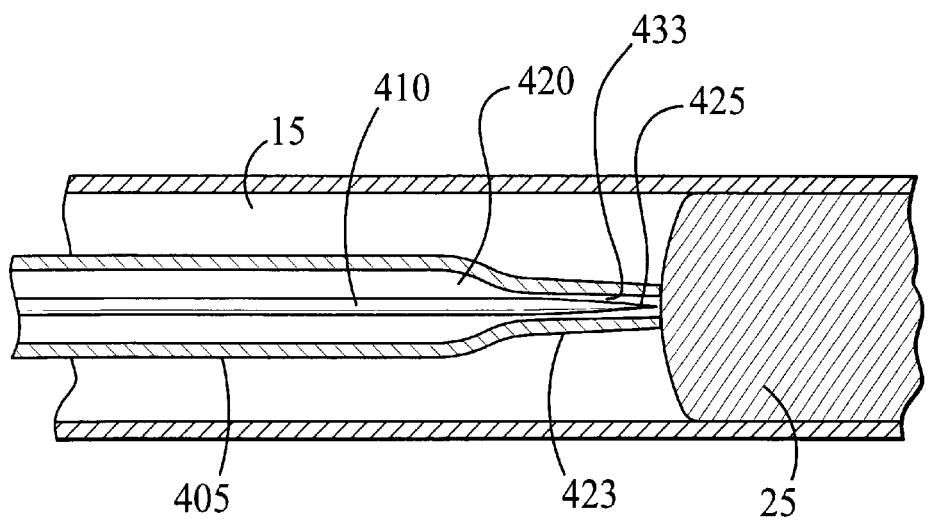
FIGS. 14 and 15 are cross-sectional side views of the treatment substance injection catheter of FIG. 13 showing insertion of the wire into an occlusion.
Figure 15:
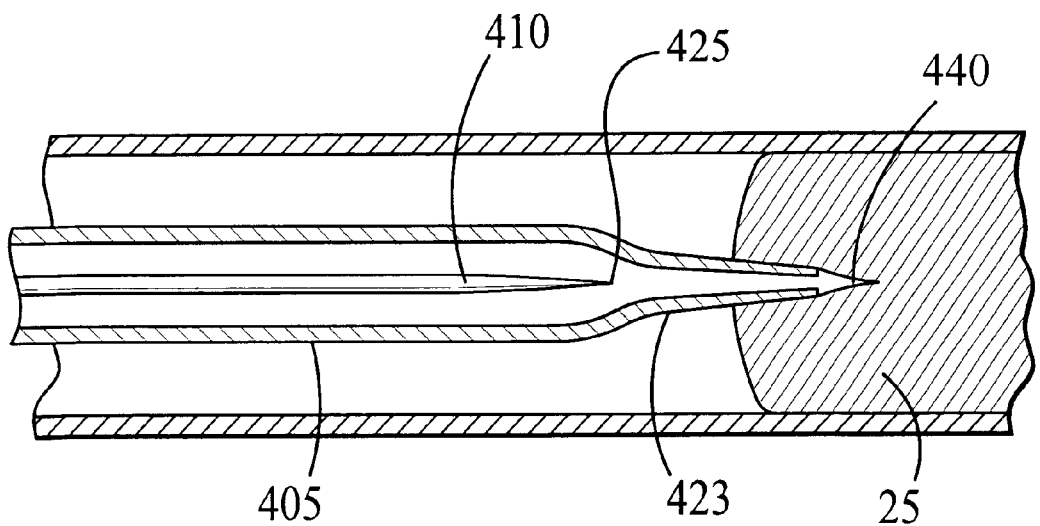

Referring to FIGS. 13 and 14, in another modification, an injection catheter system 400 includes a tubular catheter 405 and a wire 410. The tubular catheter 405 includes a hub 415 at a proximal end and a lumen 420 that runs the length of the tubular catheter. The distal end of the tubular catheter has a tapered end 423. The wire 410 includes a sharpened point 425 at its distal end 430 and is configured to be delivered through the tubular catheter 405. The outer diameter of the wire 410 is selected to be less than the diameter of a lumen 433 of the tapered end 423 so that the wire will fit snuggly within the lumen 433 but not so snug that there is difficulty in advancing the wire through the lumen. At its proximal end, the wire 410 includes a handle 435 or other grasping implement for the physician to advance and withdraw the wire.

In use of the system 400, the physician first inserts the tubular catheter 405 into the vasculature and advances the catheter to the occlusion 25. The physician then inserts the wire 410 into the hub 415 and advances the wire 410 through and out of the tapered end 423 until the sharpened point 425 contacts the occlusion 25. The physician then gently inserts the sharpened point 425 into the occlusion to form a channel 440. By further advancement of the wire 410 the channel 440 can be lengthened. To inject a treatment substance into the channel 440 to treat the occlusion 25, the physician then advances the tubular catheter 405 over the wire 410 such that the tapered end 423 follows the wire into the channel. Simultaneously the wire can be withdrawn, which leaves the tapered end 423 in the channel 440 in the occlusion 25. The physician then connects a syringe or I.V. bag (not shown) containing the treatment substance to the hub 415 and infuses the treatment substance into the occlusion 25. After delivery of the treatment substance, the tubular catheter 405 is withdrawn.

The catheters described above can be fabricated using any biocompatible polymer, such as medical grade polyethylene, polypropylene, polyurethane, and nylon. The catheters can be braided or nonbraided. The braiding material can be a metal, such as stainless steel, or a synthetic fiber, such as Kevlar. The wires used to form the channel in the occlusion and advance the plugs can be made from any biocompatible material, such as stainless steel.

Figure 16:
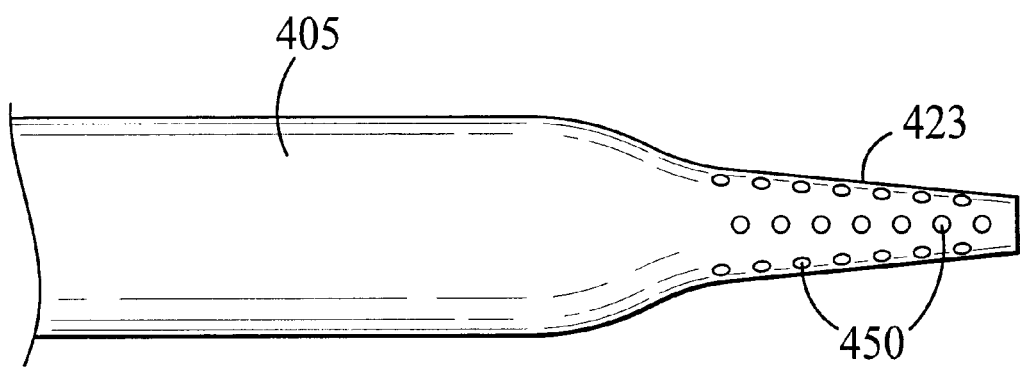
FIG. 16 is a side view of a tapered tip of the catheter of FIG. 13 with the tip having eye holes.

A number of embodiments of the invention have been described. Nevertheless, it will be understood that various modifications may be made without departing from the spirit and scope of the invention. For example, referring to FIG. 16, the tapered end 423 of the tubular catheter 405 can include eye holes 450 along its length and around its circumference to permit delivery of the treatment substance along the entire length of the channel 440 in the occlusion 25 when the tapered end 423 is deployed in the occlusion.

Figure 17:
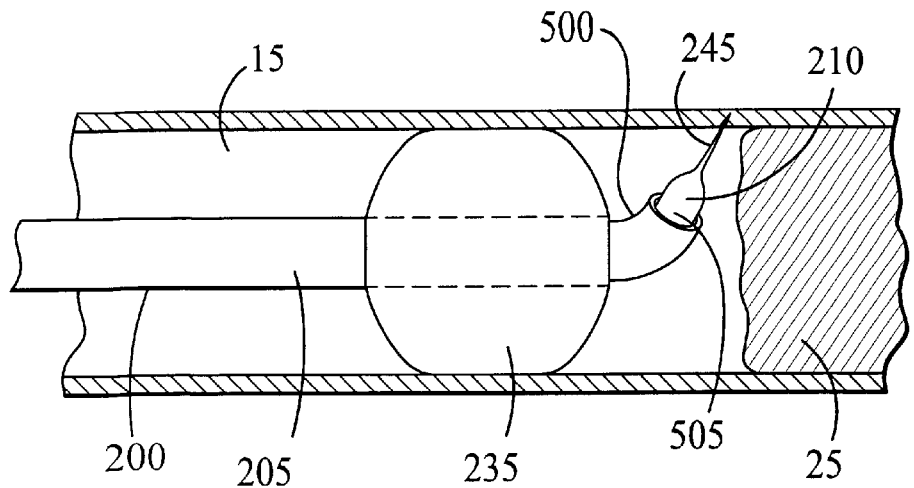
FIG. 17 is a side view of the treatment substance delivery catheter system of FIG. 7 having a curved sheath and/or wire.

Although the treatment substances can be delivered within the lumen of the tubular vessel, the treatment substances also can be delivered into or against the wall of the tubular vessel. For example, referring to FIG. 17, in another embodiment, the injection catheter system 200 can be modified to such that the sheath 215 has a curved distal end 500 and/or the wire 210 has a curved distal tip 505 such that the sharpened end 245 of the wire is directed into the wall of the tubular vessel. Advancing the wire 210 causes the sharpened end 245 to create an opening 510 in the wall of the tubular vessel. One or more treatment substances then can be inserted into the opening 510 in the wall of the tubular vessel to treat the occlusion 25 as described above.

Figure 18:
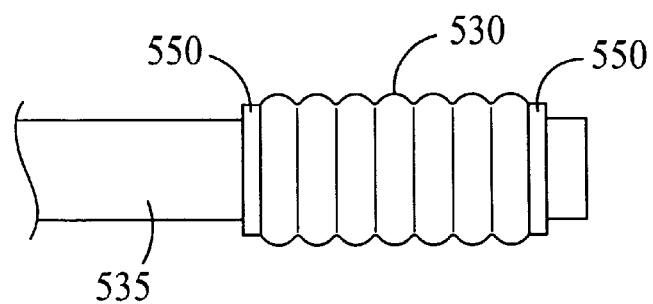
FIG. 18 is a side view of a coated stent mounted to a balloon catheter.
Figure 19:
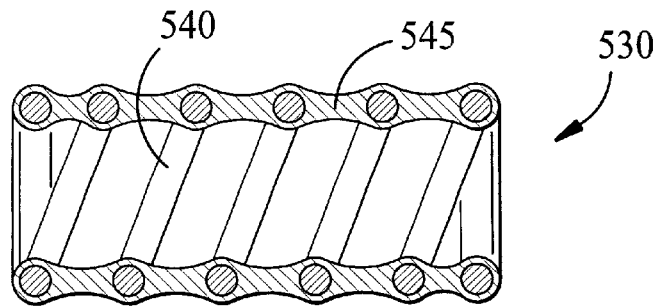
FIG. 19 is a cross-sectional side view of the coated stent of FIG. 18.
Figure 20:
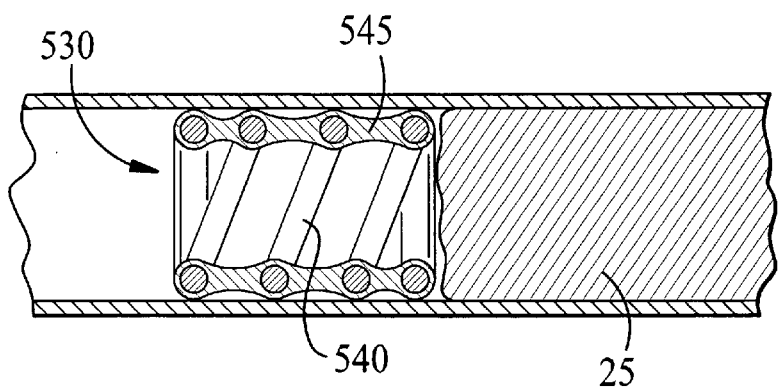
FIG. 20 is a cross-sectional side view of the coated stent of FIG. 18 deployed in an artery adjacent to an occlusion.

Although the treatment substance can be delivered and formed in situ, a treatment substance can be delivered in a completed form against the wall of the tubular vessel. For example, referring to FIGS. 18–20, an expandable treatment stent 530 that is deliverable over a balloon catheter 535 includes a stent or wire component 540 and a treatment or coating component 545. The coating component 545 can include any combination of the treatment substances described above and be in the form of, for example, a fabric, a wrap, a braid or a weave around, through, or on the wire component 540. The coating component 545 also can be dip coated on the wire component 540. Inflating a balloon 550 of the balloon catheter 535 presses the coating component 545 against the inside wall of the tubular vessel so that the materials comprising the coating component are releasable to treat the occlusion 25.

Figure 21:
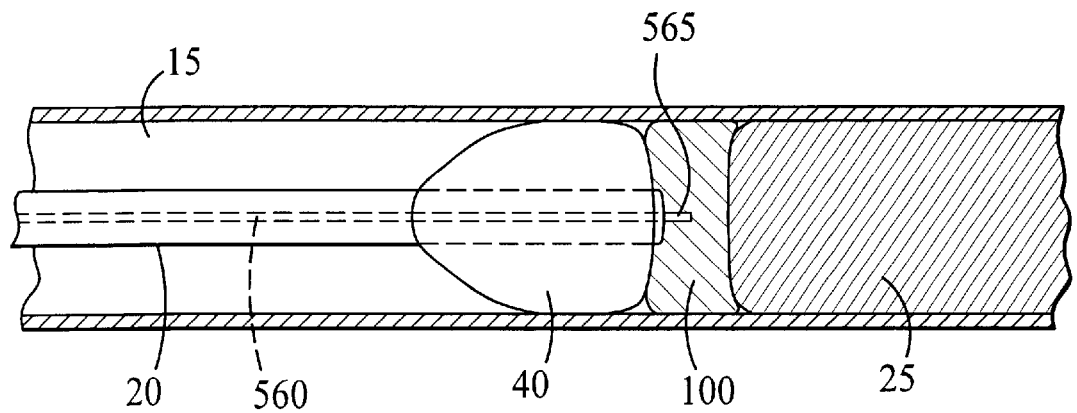
FIG. 21 is a side view of the treatment substance delivery catheter system of FIG. 7 through which a heating catheter is delivered for heating a heat curable material within a tubular vessel.

In another embodiment, a heat curable material can be used in place of the light curable material. For example, referring to FIG. 21, the layer of substance 100 can include a heat curable material and the catheter 20 is used to deliver a heat treatment catheter 560, which can be configured to produce a heating effect, into or adjacent to the layer of substance. The heat treatment catheter 560 can include a heating element 565 at the distal end of the heat treatment catheter and the catheter 560 uses RF heating to heat the element and produce a heating effect. The heating element instead may be a copper coil that is heated by resistive heating to produce a heating effect.

Also, while the above examples have been directed to treatment of occlusions in an artery, the devices and methods can be applied to any occlusion in any tubular vessel, such as the tubular vessels of the gastrointestinal tract or the urinary tract. Accordingly, other embodiments are within the scope of the following claims.

What is claimed is:

1. A catheter system for delivering a treatment substance into an occlusion in a lumen of a tubular vessel, the catheter system comprising:

a tubular catheter having a lumen passing between a proximal end and a distal end;

a wire having a distal end with a sharpened tip, the wire configured to be passed through the tubular catheter to create a channel in the occlusion;

a sheath enclosing the wire to prevent the wire from puncturing the catheter, wherein the sheath is configured to move independently of the wire to expose the distal end of the wire; and a treatment substance for delivery through the tubular catheter into the occlusion to treat the occlusion.

2. The catheter system of claim 1, wherein the treatment substance comprises an angiogenesis agent.

3. The catheter system of claim 1, wherein the treatment substance comprises an occlusion dissolving agent.

4. The catheter system of claim 1, wherein the treatment substance comprises an anti-restenosis agent.

5. The catheter system of claim 1, wherein the treatment substance comprises an inflammatory agent.

6. The catheter system of claim 1, wherein the wire includes a proximal end having a gripping member.

7. The catheter system of claim 1, wherein the tubular catheter includes a distal end having a tapered tip.

8. The catheter system of claim 7, wherein the tapered tip has an inner diameter that is larger than an outer diameter of the wire.

9. The catheter system of claim 7, wherein the tapered tip has at least one eye hole passing through a wall of the tubular catheter.

\* \* \* \* \*